US008557025B2

United States Patent
Grahl et al.

(10) Patent No.: US 8,557,025 B2
(45) Date of Patent: Oct. 15, 2013

(54) GENERATING OXYGEN IN HOSPITALS

(75) Inventors: Matthias Grahl, Munich (DE); Philippe Sage, Lisle sur Tarn (FR); Alfred Bolkart, Munich (DE); Paul Leitgeb, Pullach (DE)

(73) Assignee: Linde AG, Munich (DE)

( * ) Notice: Subject to any disclaimer, the term of this patent is extended or adjusted under 35 U.S.C. 154(b) by 192 days.

(21) Appl. No.: 13/048,114

(22) Filed: Mar. 15, 2011

(65) Prior Publication Data

US 2011/0226126 A1    Sep. 22, 2011

(30) Foreign Application Priority Data

Mar. 16, 2010   (DE) .................... 10 2010 011 584

(51) Int. Cl.
*B01D 53/047*   (2006.01)
(52) U.S. Cl.
USPC ................... 95/130; 96/111; 128/205.12
(58) Field of Classification Search
USPC ............ 95/96, 130; 96/111, 121; 128/204.18, 128/205.12
See application file for complete search history.

(56) References Cited

U.S. PATENT DOCUMENTS

| | | | |
|---|---|---|---|
| 5,415,683 A | | 5/1995 | Leavitt |
| 6,010,555 A | * | 1/2000 | Smolarek et al. ............. 95/98 |
| 6,143,056 A | * | 11/2000 | Smolarek et al. ............. 95/96 |
| 6,394,089 B1 | * | 5/2002 | Cantrill et al. ........... 128/205.12 |
| 6,712,877 B2 | * | 3/2004 | Cao et al. ........................ 95/10 |
| 7,294,170 B2 | * | 11/2007 | Richey et al. ...................... 95/8 |
| 2002/0014159 A1 | * | 2/2002 | Tatsumi et al. ................ 96/130 |
| 2009/0095154 A1 | | 4/2009 | Barone |
| 2009/0107500 A1 | | 4/2009 | Edwards |

FOREIGN PATENT DOCUMENTS

EP    1245267 A1    10/2002

OTHER PUBLICATIONS

European Search Report completed May 31, 2011 in European Application No. 11 002147.4.

* cited by examiner

*Primary Examiner* — Frank Lawrence, Jr.
(74) *Attorney, Agent, or Firm* — Millen, White, Zelano & Branigan, P.C.

(57) ABSTRACT

An arrangement for generating oxygen in a facility is described, which arrangement has at least one unit for generating medical air (V, R), a vacuum system (VS), and a PSA unit (A), which serves to generate an oxygen product stream. According to the invention, the PSA unit (A) and the vacuum system (VS) are interconnected in such a way that the adsorber or adsorbers of the PSA unit (A) can be regenerated by means of the vacuum system (VS), and/or the unit for generating medical air (V, R) is connected to the PSA unit (A) in such a way that at least a subsidiary stream (2) of the generated medical air is delivered as feed gas to the PSA unit (A).

23 Claims, 1 Drawing Sheet

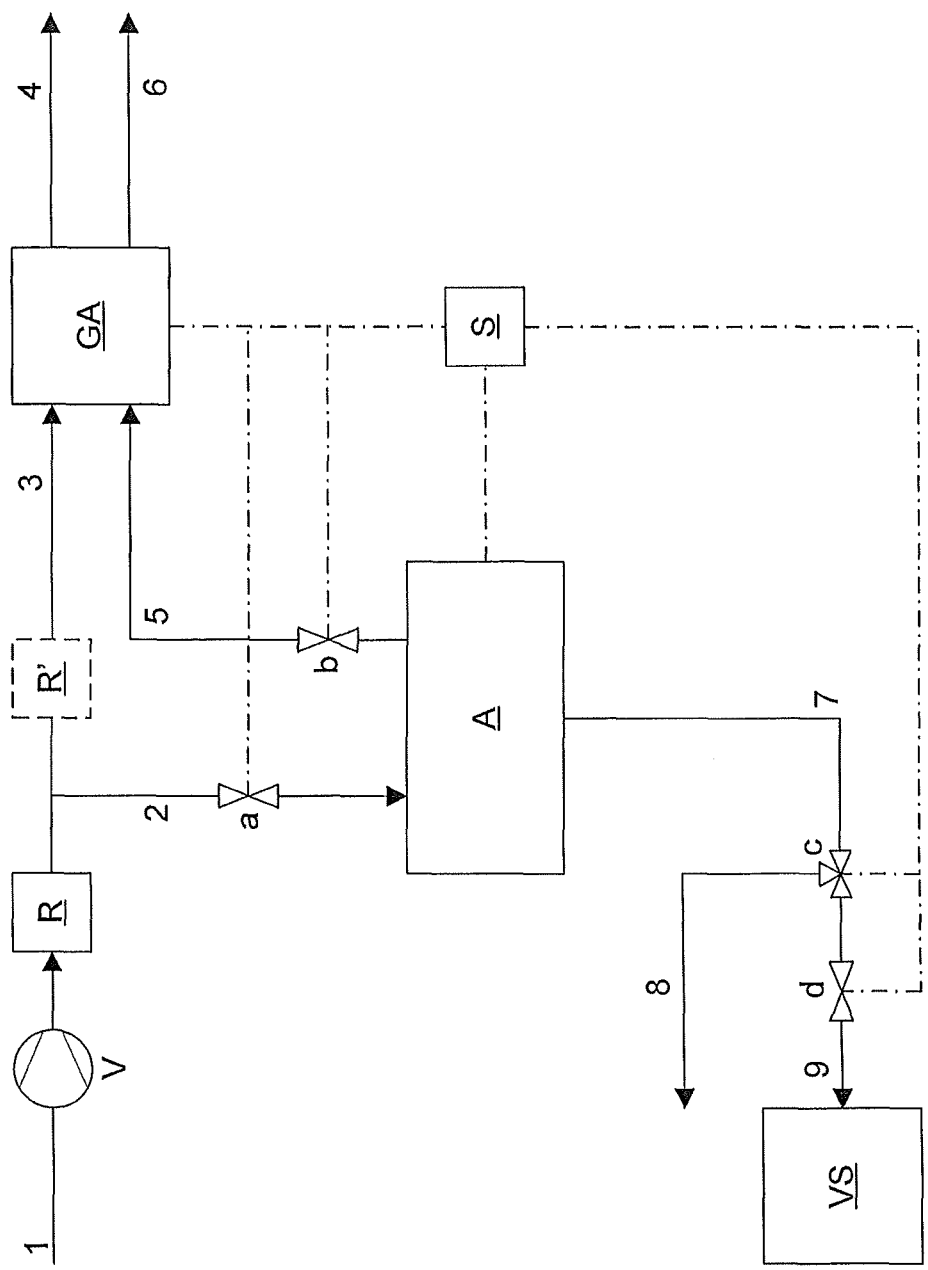

GENERATING OXYGEN IN HOSPITALS

The invention relates to an arrangement for generating oxygen in a facility, which arrangement has at least one unit for generating medical air and a vacuum system.

The invention further relates to a method for operating such an arrangement.

The word "facility" is to be understood hereinbelow as meaning any installation or facility, particularly hospitals, mobile (emergency) hospitals, outpatient clinics, general practices, wellness centres, etc., in which oxygen is generated and in which there is a vacuum system. The word "facility" is also to be understood as including (mobile) appliances which are used particularly in the homecare sector and which, for example, can be attached to a wheelchair. Moreover, the word "facility" is also to be understood as including production sites, (industrial) installations, etc., in which oxygen is generated. The use for which the generated oxygen is intended is immaterial here.

The infrastructure of a modern hospital comprises, among other things, supplying the patient with what is called "medical air", with oxygen-enriched air and with pure oxygen. The term "medical air" is usually understood as a gas mixture which has ca. 20% oxygen and ca. 80% nitrogen and which meets applicable specifications and/or regulations in respect of other components such as water and carbon monoxide. Moreover, the infrastructure of a hospital generally comprises a vacuum system. This is a system which, by means of vacuum pumps and buffer tanks in a conduit system, maintains a vacuum that is used in the hospital for all suction applications, e.g. in operating theaters.

Medical air is either generated directly on site, the main method steps being compression, purification and analysis of air, or, if used in smaller quantities, is supplied in compressed-gas canisters.

In countries with good infrastructure, hospitals are generally supplied with oxygen by delivery of liquid oxygen and by means of a liquid tank which is arranged in or near the hospital and to which an evaporator is assigned. By contrast, in developing countries with poor infrastructure, oxygen is widely generated on site with the aid of small PSA (Pressure Swing Adsorption) installations. Installations of this kind, however, consume considerable energy and require a high level of maintenance, such that the oxygen generated with these installations is not competitive in cases where inexpensive liquid oxygen is available. An oxygen supply system of this kind with a plurality of PSA installations is disclosed in EP-A 1245267.

VPSA (Vacuum Pressure Swing Adsorption) installations have long been used as so-called on-site installations for generating oxygen and have a very favorable energy consumption. However, in small installations, which are to be understood hereinbelow as installations with a capacity of less than 100 Nm$^3$/h and which are of the kind needed for supplying hospitals, the higher investment costs, resulting from the additionally required vacuum pump and from an increased need for adsorber, mean that they have not as yet become widely used.

The solutions found in the prior art for on-site generation of oxygen have the following disadvantages: they entail relatively high investment costs, have poor consumption figures and require considerable additional maintenance. Legal provisions generally require redundancy of the systems required for the on-site generation of oxygen. This further increases the necessary investment costs.

An object of the present invention is to make available an arrangement of the type in question for generating oxygen in a facility and a method of the type in question for operating such an arrangement, said arrangement and said method avoiding the aforementioned disadvantages.

Upon further study of the specification and appended claims, other objects and advantages of the invention will become apparent.

These objects are achieved by an arrangement for generating oxygen in a facility, in which the PSA unit and the vacuum system are interconnected in such a way that the adsorber or adsorbers of the PSA unit can be regenerated by means of the vacuum system.

The method according to the invention for operating the arrangement according to the invention is characterized in that the PSA unit is operated at an adsorption pressure of between 1.3 and 12 bar, preferably of between 2 and 8 bar, and/or at a desorption pressure of between 0.05 and 0.9 bar, preferably of between 0.1 and 0.6 bar.

Further advantageous embodiments of the arrangement according to the invention for generating oxygen in a facility and of the method according to the invention for operating such an arrangement are the subject matter of the dependent patent claims and are characterized in that

- the generated oxygen product stream has a purity of at least 80%, preferably of at least 90%,
- if the facility has at least one unit for gas analysis, the unit for gas analysis is connected to the product side of the PSA unit,
- additional means are provided for delivering air as feed gas for the PSA unit,
- the arrangement is assigned at least one storage tank, which serves in particular for storage of liquid oxygen,
- the arrangement is designed in such a way that it is mobile, and
- in the event of an at least partial failure of the vacuum system, the PSA unit is not regenerated by means of the vacuum system and is instead operated at a desorption pressure of between 1.01 and 1.5 bara, preferably of between 1.01 and 1.1 bara.

The invention is based on the concept of operating a PSA installation or unit by using as far as possible the existing infrastructure of a hospital. The interconnection according to the invention of PSA unit and vacuum system makes it possible to regenerate the PSA unit or the adsorber(s) thereof under vacuum conditions. The advantages and disadvantages of vacuum regeneration are known to a person skilled in the art. Since the advantages can be obtained more or less at no cost in the present case, because the vacuum system required for the vacuum regeneration is of course already present, considerable improvements are achieved in respect of the required investment costs and operating costs.

Further advantages are achieved if, in addition, the unit for generating medical air, and belonging to the infrastructure of a hospital, is chosen as the source of the air stream delivered to the PSA unit, since the previously required pre-purification of the feed air delivered to the PSA unit can be omitted. Furthermore, provision does not have to be made for separate compression of the feed air, since this is generally already provided for in the unit for generating medical air.

Hospitals usually have a unit for gas analysis. According to one embodiment of the arrangement according to the invention, this unit can be configured or developed in such a way that it can also be used for the analysis of the oxygen product stream generated in the PSA unit. As a result, it is not necessary to provide a separate analysis unit for the oxygen product stream.

BRIEF DESCRIPTION OF THE DRAWINGS

The arrangement according to the invention, the method according to the invention and other embodiments of the arrangement and of the method are explained in greater detail below with reference to the illustrative embodiment shown in the drawing. Various other features and attendant advantages of the present invention will be more fully appreciated as the same becomes better understood when considered in conjunction with the accompanying drawing wherein:

The FIGURE illustrates an embodiment of the invention.

By way of line 1, (ambient) air is delivered to a unit for generating medical air, as is usually provided in hospitals. This unit for generating medical air consists of a single-stage or multi-stage compressor unit V and of a downstream purifier unit R. The air is compressed to a pressure of between 4 and 12 bar by means of the compressor unit V, and undesired components, in particular water, carbon monoxide, carbon dioxide and if appropriate nitrogen oxides are then removed from the air in the purifier unit R. A first subsidiary stream of the medical air generated in this way is introduced through the line sections 3 and 4 into the line network for medical air. Before being introduced into the line network, the medical air is analysed by means of a corresponding analysis unit GA.

A second subsidiary stream 2 of the medical air is delivered as feed stream to the PSA unit A. The PSA unit A usually has two or more adsorbers, which are arranged in parallel and which run through adsorption and regeneration phases alternately and/or sequentially. In principle, however, the PSA unit A can also consist of just one adsorber and of additional buffer tanks. The PSA unit A is advantageously operated at an adsorption pressure of between 1.3 and 12 bar, preferably of between 3 and 8 bar, and/or at a desorption pressure of between 0.05 and 0.9 bar, preferably of between 0.1 and 0.6 bar.

All the parameters of the PSA unit A are to be chosen such that the generated oxygen product stream 5 has a purity of at last 80%, preferably of at least 90%.

The oxygen product stream generated in the PSA unit A is delivered by way of the line sections 5 and 6 to the oxygen line network of the hospital. By means of the above-described analysis unit GA, this oxygen product stream can also undergo gas analysis.

The particular requirements placed on the purity of oxygen used in hospitals can be satisfied by the use of medical air.

In contrast to the previous solutions for on-site generation of oxygen in hospitals by the PSA technique, vacuum regeneration is now performed by means of the vacuum system present in the hospital. Thus, the comparatively high adsorption pressure of a PSA technique is combined with the vacuum regeneration of a VPSA technique.

The residual-gas side of the PSA unit A is connected to the hospital's own vacuum system VS by way of the line sections 7 and 9. The vacuum system VS generally has, among other things, several vacuum pumps and buffer tanks.

At the start of the desorption or regeneration phase, desorbed gas is removed through the line sections 7 and 8 via a corresponding exhaust gas line, preferably to the environment, until atmospheric pressure is reached. After the three-way valve c has been switched, the PSA unit A can be regenerated via the line sections 7 and 9 to the desired subatmospheric regeneration pressure by means of the vacuum system VS.

In the line section 9, an additional control valve d can be provided which is used to even out the residual gas stream drawn off via the vacuum system VS, as a result of which an undesirably sharp rise in pressure in the vacuum system VS of the hospital can be effectively avoided.

Advantageously, the available vacuum performance is detected automatically on the basis of the desorption pressure. Depending on this, a maximum removal of product is (automatically) set. Thus, less product or oxygen is removed at a higher regeneration pressure and more oxygen is removed at a lower regeneration pressure.

In addition to the two valves c and d mentioned, the feed gas line 2 and the product line 5 are also generally provided with valves a and b, which serve to regulate the air quantity delivered to the PSA unit A via line 2 and also the oxygen quantity drawn off from the PSA unit A via line 5. All the valves, the PSA unit A and, optionally, the gas analysis unit GA are controlled by a control unit S, as is indicated by the dot-and-dash lines.

Alternatively to the purifier unit R shown in the FIGURE and located downstream of the compressor unit V, a purifier unit R' can be provided in the line section 3. In this case, the PSA unit A is to be designed, or the adsorbers used in it chosen, such that undesired components of the feed air stream delivered via line 2 to the PSA unit A can be separated off to a sufficient extent.

A further embodiment (not shown in the FIGURE) of the arrangement according to the invention for generating oxygen is characterized in that the air delivered to the PSA unit A is compressed by means of a separate compressor unit not assigned to the unit for generating medical air. In such a case, it may be expedient, with regard to the required energy consumption, to choose a lower adsorption pressure and, if appropriate, recompress the oxygen product stream drawn off from the PSA unit A via line 5.

Moreover, the arrangement can be assigned a storage tank (not shown in the FIGURE) which serves for the storage of liquid oxygen. This design is of advantage, for example, when the PSA unit is intended to ensure only the basic oxygen demand, while the peak demand is covered by the oxygen stored in the storage tank.

The PSA unit A is operated, for example, with an adsorption pressure of 3 bara and a desorption pressure of 0.45 bara; the product quantity is 10 $Nm^3/h$, the oxygen content 93%. Such a process with vacuum regeneration has a substantially higher yield than a PSA process, namely ca. 70% as compared with ca. 40% in a PSA process. Provision of the product quantity of 10 $Nm^3/h$ requires only an air quantity of 62 $Nm^3/h$, which has to be taken from the hospital's own network for medical air. The required suction power for the vacuum regeneration at the chosen desorption pressure of 0.45 bara is ca. 60 eff. $m^3/h$.

The investments required for the oxygen-generating arrangement according to the invention and for the method according to the invention are confined to the PSA unit and to corresponding pipes for connection to the hospital's own network for medical air and vacuum system VS. Additional machines and apparatus are not needed for the arrangement according to the invention and the method according to the invention.

It has been found that, in a method with high adsorption pressure plus vacuum regeneration, it is possible to achieve optimal operation without having to assist the regeneration by flushing with at least some of the product stream. Instead, after the pressure equalization phase and dump phase, sufficient oxygen is still present at the adsorber head to achieve a sufficient flushing action. The omission of a flush cycle simplifies the piping on the product side of the PSA unit A and thus increases the reliability thereof. The size of the necessary adsorbers can also be substantially reduced compared to a conventional PSA process. Moreover, the level of maintenance needed for the PSA unit A is much less than for a separate PSA or VPSA installation, since maintenance is confined exclusively to the actual adsorber unit and basically to a few switching valves.

As a development of the method according to the invention, it is proposed that, in the event of an at least partial failure of the vacuum system VS, the PSA unit A is not regenerated by means of the vacuum system VS and is instead operated at a desorption pressure slightly above the atmospheric air pressure, that is to say between 1.01 and 1.5 bara, preferably between 1.01 and 1.1 bara.

In the event of a breakdown of the vacuum system VS, the PSA unit A is operated purely as a PSA installation. In this operating mode, however, the quantity of oxygen that can be generated is greatly reduced.

As a development of the arrangement according to the invention for generating oxygen in a facility, it is proposed that the arrangement be designed in such a way that it is mobile. The word "mobile" is to be understood here as meaning that the arrangement is transportable, for example can be transported in a container or by truck. Such an embodiment developing the arrangement according to the invention for generating oxygen in a facility is expedient in particular if the arrangement is intended to be used in a mobile (emergency) hospital, for example. In this connection, the arrangement according to the invention is also preferably designed in such a way that it meets the requirements in respect of temperature, air humidity, sand, and transport by land, air and sea, etc.

Regardless of whether the facility in which the arrangement according to the invention for generating oxygen is intended to be used is newly built or has already existed for some time, the method for installing or assembling the arrangement according to the invention requires that the PSA unit and the vacuum system be interconnected in such a way that the adsorber or adsorbers of the PSA unit can be regenerated by means of the vacuum system, and/or the unit for generating medical air is connected to the PSA unit in such a way that at least a subsidiary stream of the generated medical air is delivered as feed gas to the PSA unit.

The arrangement according to the invention for generating oxygen in a facility now permits a reduction in the investment costs needed for on-site generation of oxygen. At the same time, the consumption figures for the generation of the oxygen and the required maintenance work can be significantly reduced compared to previous solutions.

In the homecare sector, where mobile devices, preferably attachable to wheelchairs, are used to supply oxygen, the arrangement according to the invention and the method according to the invention, for operating an arrangement for generating oxygen, afford considerable advantages over the devices belonging to the prior art.

The entire disclosure[s] of all applications, patents and publications, cited herein and of corresponding German Application No. 10 2010 011 584.3, filed Mar. 16, 2010 are incorporated by reference herein.

The preceding examples can be repeated with similar success by substituting the generically or specifically described reactants and/or operating conditions of this invention for those used in the preceding examples.

The invention claimed is:

1. A system comprising comprising:
at least one unit for generating medical air (V, R), a PSA unit (A) which serves to generate an oxygen product stream, and a facility comprising a line network for medical air, an oxygen line network, and a vacuum system (VS),
wherein said at least one unit for generating medical air (V, R) is connected to the line network for medical air in such a way that a first subsidiary stream generated medical air is delivered from said at least one unit for generating medical air (V, R) to said line network for medical air,
said at least one unit for generating medical air (V, R) is connected to said PSA unit (A) in such a way that at least a second subsidiary stream (2) of generated medical air is delivered as feed gas to said PSA unit (A), and
said PSA unit (A) and said vacuum system (VS) are interconnected in such a way that the adsorber or adsorbers of said PSA unit (A) can be regenerated by means of said vacuum system (VS).

2. A system according to claim 1, wherein the generated oxygen product stream (5) has a purity of at least 80%.

3. A system according to claim 1, wherein the generated oxygen product stream (5) has a purity of at least 90%.

4. A system according to claim 1, wherein the facility further comprises at least one unit for gas analysis (GA) which is connected to the product side of the PSA unit (A).

5. A system according claim 1, further comprising additional means are provided for delivering air as feed gas for the PSA unit (A).

6. A system according to claim 1, further comprising at least one storage tank.

7. A system according to claim 1, wherein the system is designed in such a way that it is mobile.

8. A method for operating a system according to claim 1, said method comprising:
generating medical air in said at least one unit for generating medical air (V, R),
removing a first subsidiary stream of generated medical air from said at least one unit for generating medical air (V, R) and introducing said first subsidiary stream into the line network for medical air of said facility, and
removing a second stream of generated medical air from said at least one unit for generating medical air (V, R) and introducing said second subsidiary stream as feed gas to said PSA unit (A),
wherein said PSA unit (A) is connected to said vacuum system (VS) of said facility in such a way that the adsorber or adsorbers of the PSA unit (A) can be regenerated by means of the vacuum system (VS).

9. A method according to claim 8, wherein the PSA unit (A) is operated at an adsorption pressure of between 1.3 and 12 bar.

10. A method according to claim 9, wherein the PSA unit (A) is operated at an adsorption pressure of between 2 and 8 bar.

11. A method according to claim 8, wherein the PSA unit (A) is operated at a desorption pressure of between 0.05 and 0.9 bar.

12. A method according to claim 11, wherein the PSA unit (A) is operated at a desorption pressure of between 0.1 and 0.6 bar.

13. A method according to claim 8, wherein the generated oxygen product stream (5) has a purity of at least 80%.

14. A method according to claim 8, wherein the generated oxygen product stream (5) has a purity of at least 90%.

15. A method according to claim 8, wherein, in the event of an at least partial failure of the vacuum system (VS), the PSA unit (A) is not regenerated by means of the vacuum system (VS) and is instead operated at a desorption pressure of between 1.01 and 1.5 bara.

16. A method according to claim 15, wherein, in the event of an at least partial failure of the vacuum system (VS), the PSA unit (A) is operated at a desorption pressure of between 1.01 and 1.1 bara.

17. A method for installing and/or assembling an arrangement according to claim 1, said method comprising:
- interconnecting the PSA unit (A) and the vacuum system (VS) in such a way that the adsorber or adsorbers of the PSA unit (A) can be regenerated by means of the vacuum system (VS), and
- connecting the unit for generating medical air (V, R) to the line network for medical air in such a way that the first subsidiary stream generated medical air is delivered from said at least one unit for generating medical air (V, R) to said line network for medical air, and
- connecting the unit for generating medical air (V R) to the PSA unit (A) in such a way that at least the second subsidiary stream (2) of the generated medical air is delivered as feed gas to the PSA unit (A).

18. A system according to claim 1, wherein said PSA unit is connected to said oxygen line network of said facility.

19. A method according to claim 8, further comprising removing a generated oxygen product stream from said PSA unit and introducing said generated oxygen product stream into the oxygen line network of said facility.

20. A method according to claim 17, further comprising connecting said PSA unit to the oxygen line network of said facility in such a way a generated oxygen product stream is delivered from said PSA unit to the oxygen line network of said facility.

21. A system according to claim 1, wherein said unit for generating medical air contains a single-stage or multi-stage compressor and purifier unit downstream of the compressor.

22. A system according to claim 1, wherein said PSA unit comprises at least two adsorbers arranged in parallel.

23. A system according to claim 6, wherein said at least one storage tank is for storage of liquid oxygen.

* * * * *